United States Patent
Asada

(10) Patent No.: US 7,998,223 B2
(45) Date of Patent: Aug. 16, 2011

(54) HAIRDYE PREPARATION COMPOSITION

(75) Inventor: Takuji Asada, Aichi-ken (JP)

(73) Assignee: Hoyu Co., Ltd., Aichi-Ken (JP)

( * ) Notice: Subject to any disclaimer, the term of this patent is extended or adjusted under 35 U.S.C. 154(b) by 0 days.

(21) Appl. No.: 12/993,219

(22) PCT Filed: Aug. 4, 2008

(86) PCT No.: PCT/JP2008/063983
§ 371 (c)(1), (2), (4) Date: Nov. 17, 2010

(87) PCT Pub. No.: WO2010/016105
PCT Pub. Date: Feb. 11, 2010

(65) Prior Publication Data
US 2011/0061178 A1    Mar. 17, 2011

(51) Int. Cl.
*A61Q 5/10* (2006.01)

(52) U.S. Cl. ............. 8/405; 8/406; 8/408; 8/431; 8/435; 8/594

(58) Field of Classification Search ............. 8/405, 406, 8/408, 431, 435, 594
See application file for complete search history.

(56) References Cited

FOREIGN PATENT DOCUMENTS

| JP | 2002-029946 | 1/2002 |
| JP | 2005-298396 | 10/2005 |
| JP | 2005-298431 | 10/2005 |
| JP | 2005298431 A * | 10/2005 |

OTHER PUBLICATIONS

"International Search Report on Patentability for International Application No. PCT/JP2008/063983," Report completed by an Authorized Officer of the Patent Cooperation Treaty on Apr. 27, 2010. 5 pages.

* cited by examiner

*Primary Examiner* — Eisa B Elhilo
(74) *Attorney, Agent, or Firm* — Seager, Tufte & Wickhem LLC

(57) ABSTRACT

A hair dye composition is provided that comprises a first agent containing an oxidation dye and an alkaline agent, and a second agent containing hydrogen peroxide, the hair dye composition being used after mixing the first agent and the second agent. The hair dye composition contains an ascorbic acid compound and the hydrogen peroxide in amounts of from 1.0 to 5.0% by mass and from 0.3 to 1.6% by mass, respectively. The alkaline agent is contained in an amount of from 3.0 to 30 mmol per 100 g of the hair dye composition.

5 Claims, 1 Drawing Sheet

|  | Example 1 | Example 6 | Example 9 | Comparative Example 6 | Comparative Example 7 |
|---|---|---|---|---|---|
| Evaluation | ++ | + | ± | - | -- |
| Photographs of skin staining | | | | | |

HAIRDYE PREPARATION COMPOSITION

FIELD OF THE INVENTION

The present invention relates to a hair dye composition, and more particularly to a hair dye composition capable of preventing skin from staining while suppressing reduced hair dye activity.

BACKGROUND OF THE INVENTION

Hair cosmetic compositions that become active upon mixing a plurality of agents are known. As an example of such hair cosmetic compositions a known hair dye composition comprises a first agent containing an oxidation dye and an alkaline agent, and a second agent containing an oxidizing agent such as hydrogen peroxide. The alkaline agent promotes the action of the oxidizing agent contained in the second agent. Further, the alkaline agent swells hair and improves the permeability of the oxidation dye into the hair. This enhances the hair dye activity. The oxidizing agent is decomposed by the action of the alkaline agent, releasing active oxygen and oxidizing the oxidation dye to develop a color.

A hair dye composition using an oxidation dye is superior in dye activity. Thus, it is not easy to remove the hair dye having dyed skin during a hair dyeing treatment process. To cope with this, a hair dye composition containing an excess amount of ascorbic acid as disclosed in Patent Document 1 is known. With the hair dye composition, during hair dyeing treatment, the excess amount of ascorbic acid prevents skin from staining without decreasing the hair dye activity of the hair dye.

However, although the hair dye composition according to the Patent Document 1 contains an excess amount of ascorbic acid, it contains relatively large amounts of an alkaline agent and an oxidizing agent in order to obtain desired hair dye activity.

Patent Document 1: Japanese Laid-Open Patent Publication No. 2002-29946

SUMMARY OF THE INVENTION

The inventor has discovered, for a hair dye composition containing an oxidation dye, a constitution that can realize desired hair dye activity and prevent skin from staining, even if the respective contents of an oxidizing agent, an alkaline agent and ascorbic acid are reduced. An objective of the present invention is to provide a hair dye composition containing an oxidation dye which can prevent skin from staining without lowering the hair dye activity.

To accomplish the objective, according to a first aspect of the present invention, a hair dye composition is provided comprising a first agent containing an oxidation dye and an alkaline agent, and a second agent containing hydrogen peroxide, the hair dye composition being used after mixing of the first agent and the second agent. The hair dye composition contains an ascorbic acid compound and the hydrogen peroxide in amounts of from 1.0 to 5.0% by mass and from 0.3 to 1.6% by mass, respectively. The alkaline agent is contained in an amount of from 3.0 to 30 mmol per 100 g of the hair dye composition.

The oxidation dye preferably contains a dye intermediate, wherein the hair dye composition preferably has a mass ratio of dye intermediate content to ascorbic acid compound content in the hair dye composition of from 0.7 to 1.0.

The ascorbic acid compound is preferably contained in the hair dye composition in an amount of from 1.2 to 4.5% by mass.

The hair dye composition preferably has a pH of from 6.5 to 9.5.

The hair dye composition preferably has a molar ratio of alkaline agent content to ascorbic acid compound content in the hair dye composition of from 0.5 to 2.8.

DETAILED DESCRIPTION OF THE PREFERRED EMBODIMENTS

Figure 1:
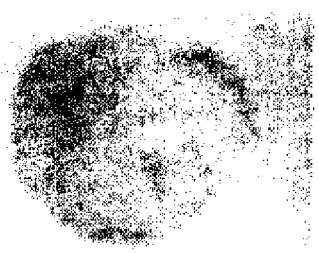
FIG. 1 shows photographs of upper arm parts to which hair dye compositions were respectively applied and then washed out.

An embodiment embodying the hair dye composition according to the present invention will be described below in detail. The hair dye composition according to the present embodiment is a two-agent-type hair cosmetic comprising a first agent and a second agent.

<First Agent>

The first agent contains an oxidation dye and an alkaline agent. The first agent contains, for example, an ascorbic acid compound. The oxidation dye develops a color due to an oxidative polymerization caused by hydrogen peroxide contained in the second agent. The oxidation dye can be classified into a dye intermediate and a coupler. The oxidation dye preferably contains a dye intermediate.

Examples of a dye intermediate include p-phenylenediamine, toluene-2,5-diamine, N-phenyl-p-phenylenediamine, 4,4'-diaminodiphenylamine, p-aminophenol, o-aminophenol, p-methylaminophenol, N,N-bis(2-hydroxyethyl)-p-phenylenediamine, 2-hydroxyethyl-p-phenylenediamine, o-chlor-p-phenylenediamine, 4-amino-m-cresol, 2-amino-4-hydroxyethylaminoanisole, 2,4-diaminophenol, and salts thereof. Of the examples of a dye intermediate, one may be used alone or two or more may be used in combination.

A coupler develops a color by coupling with a dye intermediate. Examples of a coupler include 5-amino-o-cresol, m-aminophenol, 5-(2-hydroxyethylamino)-2-methylphenol, m-phenylenediamine, 2,4-diaminophenoxyethanol, toluene-3,4-diamine, 2,6-diaminopyridine, diphenylamine, N,N-diethyl-m-aminophenol, phenyl methyl pyrazolone, and salts thereof. Of the examples of a coupler, one may be used alone or two or more may be used in combination.

An oxidation dye provides various hair color tones. An oxidation dye is preferably constituted of at least one selected from the examples of a dye intermediate, and at least one selected from the examples of a coupler. The first agent may contain, for example, at least one selected from oxidation dyes listed in "Iyakubugaihin Genryo Kikaku (Japanese Standards of Quasi-drug Ingredients)" (published in Jun. 1991, by Yakuji Nippo Limited) and direct dyes.

The content of an oxidation dye in the hair dye composition is preferably 0.02 to 25% by mass, and more preferably 0.12 to 15% by mass. If the content of an oxidation dye is less than 0.02% by mass, sufficient hair dye activity may not be obtained. On the other hand, if the content of an oxidation dye exceeds 25% by mass, the hair dye activity does not increase further, and consequently it is not economical.

The content of a dye intermediate in the hair dye composition is preferably 0.01 to 15% by mass, and more preferably 0.1 to 10% by mass. If the content of a dye intermediate is less than 0.01% by mass, sufficient hair dye activity may not be obtained. On the other hand, if the content of a dye intermediate exceeds 15% by mass, the hair dye activity does not increase further, and consequently it is not economical.

The content of a coupler in the hair dye composition is preferably 0.01 to 10% by mass, and more preferably 0.02 to 5% by mass. If the content of a coupler is less than 0.01% by mass, sufficient hair dye activity may not be obtained. On the other hand, if the content of a coupler exceeds 10% by mass, the hair dye activity does not increase further, and consequently it is not economical.

The alkaline agent promotes the action of hydrogen peroxide contained in the second agent. Further, the alkaline agent swells hair to improve the permeability of the dye into the hair. They contribute to improvement in the hair dye activity. Examples of an alkaline agent include ammonia, an alkanolamine, an organic amine, an inorganic alkali, a basic amino acid, and salts thereof. Examples of an alkanolamine include monoethanolamine, isopropanolamine, 2-amino-2-methylpropanol, diethanolamine, and triethanolamine. Examples of an organic amine include 2-amino-2-methyl-1,3-propanediol and guanidine. Examples of an inorganic alkali include sodium hydroxide, potassium hydroxide, sodium carbonate, and potassium carbonate. Examples of a basic amino acid include arginine and lysine. Examples of a salt include an ammonium salt. Of the examples of an alkaline agent, one may be used alone or two or more may be used in combination.

The alkaline agent is contained in an amount of from 3.0 to 30 mmol, and preferably 10 to 30 mmol per 100 g of the hair dye composition. If the content of an alkaline agent per 100 g of the hair dye composition is less than 3.0 mmol, the hair dye activity decreases. On the other hand, if the content of an alkaline agent per 100 g of the hair dye composition exceeds 30 mmol, skin staining cannot be sufficiently prevented.

The ascorbic acid compound is used to prevent skin from staining. An ascorbic acid compound may be contained in the second agent. Examples of an ascorbic acid compound include ascorbic acid, erythorbic acid, salts thereof, and derivatives thereof. Examples of the salts of ascorbic acid and erythorbic acid include sodium ascorbate, potassium ascorbate, calcium ascorbate, ammonium ascorbate, monoethanolamine ascorbate, diethanolamine ascorbate, and sodium erythorbate. Examples of the derivatives of ascorbic acid and erythorbic acid include disodium ascorbyl sulfate, disodium erythorbyl sulfate, magnesium ascorbyl phosphate, ascorbyl palmitate, ascorbyl stearate, ascorbyl dipalmitate, ascorbyl tetra 2-hexyldecanoate, ascorbyl myristate, ascorbyl laurate, ascorbyl acetate, ascorbyl propionate, ascorbyl tartrate, ascorbyl citrate, ascorbyl succinate, ascorbyl benzoate, potassium ascorbyl tocopheryl phosphate, ethyl ascorbic acid, allantoin ascorbate, chitosan ascorbate, methylsilanol ascorbate, ascorbyl tetradecylhexyl, aminopropyl ascorbyl phosphate, ascorbic acid polypeptide, ascorbyl glucoside, and ascorbyl methylsilanol pectinate. Among the ascorbic acid compounds, especially preferable are ascorbic acid, erythorbic acid, and salts thereof.

The content of an ascorbic acid compound in the hair dye composition is 1.0 to 5.0% by mass, preferably 1.2 to 4.5% by mass, and more preferably 1.2 to 3.0% by mass. If the content of the ascorbic acids is less than 1% by mass, skin staining cannot be sufficiently prevented. If the content of the ascorbic acids exceeds 5.0% by mass, the hair dye activity decreases.

In a hair dye composition prepared by mixing the first and second agents at a predetermined ratio, the mass ratio of the content of the dye intermediate to the content of the ascorbic acid compound (dye intermediate/ascorbic acid compound) is preferably 0.7 to 1.0, and more preferably 0.7 to 0.9. By limiting the mass ratio of the dye intermediate content to the ascorbic acid compound content to the range, the effect of preventing skin from staining is further improved.

In a hair dye composition prepared by mixing the first and second agents at a predetermined ratio, the molar ratio of the content of the alkaline agent to the content of the ascorbic acid compound (alkaline agent/ascorbic acid compound) is preferably 0.5 to 2.8, and more preferably 1.0 to 2.8. By limiting the molar ratio of the alkaline agent content to the ascorbic acid compound content to the range, the effect of preventing skin from staining is further improved.

The first agent may contain according to need in addition to the aforedescribed ingredients, for example, water, a water-soluble polymer, an oil component, a polyhydric alcohol, a surfactant, a sugar, an antiseptic, a chelating agent, a stabilizer, a pH adjuster, a plant extract, a crude drug extract, a vitamin, a fragrance, an antioxidant other than those described above, and an ultraviolet absorbent.

Water functions as a solubilizer for the respective ingredients. Examples of a water-soluble polymer include an anionic polymer, a cationic polymer, a nonionic polymer, and an amphoteric natural or synthetic polymer.

An oil component imparts a moist feel to hair. The first agent therefore preferably contains an oil component. Examples of an oil component include a fat and oil, a wax, a higher alcohol, a hydrocarbon, a higher fatty acid, an alkyl glyceryl ether, an ester, and a silicone.

Examples of a fat and oil include an olive oil, a camellia oil, a shea butter, an almond oil, a safflower oil, a sunflower oil, a soybean oil, a cottonseed oil, a sesame oil, a corn oil, a rapeseed oil, a rice bran oil, a rice germ oil, a grape seed oil, an avocado oil, a macadamia nut oil, a castor oil, a coconut oil, and an evening primrose oil. Examples of a wax include a beeswax, a candelilla wax, a carnauba wax, a jojoba oil, and a lanolin. Examples of a higher alcohol include cetyl alcohol (cetanol), 2-hexyldecanol, stearyl alcohol, isostearyl alcohol, cetostearyl alcohol, oleyl alcohol, arachyl alcohol, behenyl alcohol, 2-octyldodecanol, lauryl alcohol, myristyl alcohol, decyl tetradecanol, and lanolin alcohol.

Examples of a hydrocarbon include a paraffin, an olefin oligomer, polyisobutene, hydrogenated polyisobutene, a mineral oil, squalane, polybutene, polyethylene, a microcrystalline wax, and a vaseline. Examples of a higher fatty acid include lauric acid, myristic acid, palmitic acid, stearic acid, behenic acid, isostearic acid, 12-hydroxystearic acid, oleic acid, and a lanolin fatty acid. Examples of an alkyl glyceryl ether include batyl alcohol, chimyl alcohol, selachyl alcohol, and isostearyl glyceryl ether.

Examples of an ester include diisopropyl adipate, isopropyl myristate, cetyl octanoate, isononyl isononanoate, octyldodecyl myristate, isopropyl palmitate, stearyl stearate, myristyl myristate, isotridecyl myristate, 2-ethylhexyl palmitate, octyldodecyl ricinoleate, a C10 to C30 fatty acid cholesteryl/lanosteryl ester, cetyl lactate, acetylated lanolin, ethylene glycol di-2-ethylhexanoate, a pentaerythritol ester of a fatty acid, a dipentaerythritol ester of a fatty acid, cetyl caprate, glyceryl tricaprylate, diisostearyl malate, and dioctyl succinate.

Examples of a silicone include dimethyl polysiloxane (dimethicone), methyl phenyl polysiloxane, decamethylcyclopentasiloxane, dodecamethylcyclohexasiloxane, dimethyl polysiloxane with a modified terminal hydroxy group, a highly polymerized silicone having an average degree of polymerization of 650 to 10,000, a polyether modified silicone, an amino modified silicone, a betaine modified silicone, an alkyl modified silicone, an alkoxy modified silicone, a mercapto modified silicone, a carboxy modified silicone, and a fluorine modified silicone. Of the examples of an oil component, one may be used alone or two or more may be used in combination.

Examples of a polyhydric alcohol include a glycol and a glycerin compound. Examples of a glycol include ethylene glycol, diethylene glycol, triethylene glycol, polyethylene glycol, propylene glycol, dipropylene glycol, isoprene glycol, and 1,3-butylene glycol. Examples of a glycerin compound include glycerin, diglycerin, and polyglycerin.

A surfactant functions as an emulsifier or a solubilizer for the respective ingredients. More specifically, a surfactant emulsifies or solubilizes a hair dye composition, adjusts the viscosity and improves the viscosity stability. Examples of a surfactant include an anionic surfactant, a cationic surfactant, an amphoteric surfactant, and a nonionic surfactant. Examples of an anionic surfactant include an alkyl ether sulfate, an alkyl sulfate, an alkenyl ether sulfate, an alkenyl sulfate, an olefin sulfonate, an alkane sulfonate, a saturated or unsaturated fatty acid salt, an alkyl or alkenyl ether carboxylate, an α-sulfone fatty acid salt, an N-acylamino acid surfactant, a phosphoric mono- or di-ester surfactant, and a sulfosuccinate. Examples of a counter ion for the anionic groups of the surfactants include a sodium ion, a potassium ion, and triethanolamine. Examples of an alkyl sulfate include sodium lauryl sulfate.

Examples of a cationic surfactant include an alkyl trimethyl ammonium salt, an alkenyl trimethyl ammonium salt, a dialkyl dimethyl ammonium salt, a dialkenyl dimethyl ammonium salt, a lanolin fatty acid amidopropyl ethyldimethyl ammonium, an alkyloyl amidopropyl dimethylamine, an alkyl pyridinium salt, and a benzalkonium salt. Examples of a counter ion for the cationic groups of the surfactants include a chloride ion, a bromide ion, an iodide ion, an alkylsulfate ion, and saccharin. Examples of an alkyl trimethyl ammonium salt include stearyl trimethyl ammonium chloride, cetyl trimethyl ammonium chloride, and lauryl trimethyl ammonium chloride. Examples of a benzalkonium salt include benzalkonium chloride.

Examples of an amphoteric surfactant include coco betaine, lauramidopropyl betaine, cocamidopropyl betaine, sodium lauroamphoacetate, sodium cocoamphoacetate, and lauryl betaine (lauryl dimethyl aminoacetate betaine).

Examples of a nonionic surfactant include a polyoxyalkylene alkyl ether, a polyoxyalkylene alkenyl ether, a polyoxyethylene (POE) sorbitan fatty acid ester, a sucrose fatty acid ester, a sorbitan fatty acid ester, an alkyl saccharide surfactant, a glycerin fatty acid ester, a POE hardened castor oil, a fatty acid alcanolamide, a polyether modified silicone, and an alkyl amine oxide. Examples of a polyoxyalkylene alkyl ether include laureth (POE lauryl ether), ceteth (POE cetyl ether), steareth (POE stearyl ether), oleth (POE oleyl ether), and pareth (POE alkyl (C12-15) ether). Of the examples of a surfactant, one may be used alone or two or more may be used in combination.

Examples of a sugar include sorbitol and maltose. Examples of an antiseptic include paraben. Examples of a chelating agent include disodium ethylenediaminetetraacetate (EDTA-2Na), 1-hydroxyethane-1,1-diphosphonic acid, and salts thereof. Examples of a stabilizer include phenacetin, 8-hydroxyquinoline, acetanilide, sodium pyrophosphate, barbituric acid, uric acid, and tannic acid. Examples of a pH adjuster include lactic acid, levulinic acid, glycolic acid, tartaric acid, malic acid, pyrrolidone carboxylic acid (PCA), succinic acid, citric acid, and glutamic acid. Examples of an antioxidant include a sulfite.

There is no particular restriction on the form of the first agent, and specific examples thereof include a liquid form, a gel form, a foam form, and a cream form. Examples of a liquid form include an aqueous solution, a dispersion liquid, and an emulsion liquid.

<Second Agent>

The second agent contains hydrogen peroxide. Hydrogen peroxide bleaches melanin contained in hair and oxidizes an oxidation dye to develop a color. The content of hydrogen peroxide in a hair dye composition is 0.3 to 1.6% by mass, and preferably 0.3 to 1.4% by mass. If the content of hydrogen peroxide is less than 0.3% by mass, the oxidation dye cannot be sufficiently oxidized. If the content of hydrogen peroxide exceeds 1.6% by mass, skin staining prevention activity is lowered.

In order to improve the stability of the hydrogen peroxide, the second agent preferably contains a stabilizer, such as ethylene glycol phenyl ether (phenoxyethanol), and 1-hydroxyethane-1,1-diphosphonic acid or a salt thereof. Examples of a salt of 1-hydroxyethane-1,1-diphosphonic acid include tetrasodium 1-hydroxyethane-1,1-diphosphonate and disodium 1-hydroxyethane-1,1-diphosphonate. The second agent may contain an ingredient that is contained in a conventional hair dye composition and does not interfere with the actions of the aforedescribed respective ingredients. The second agent may contain, for example, an ingredient contained in the first agent excluding an oxidation dye and an alkaline agent.

There is no particular restriction on the form of the second agent, and specific examples thereof include a liquid form, a gel form, a foam form, and a cream form. Examples of a liquid form include an aqueous solution, a dispersion liquid, and an emulsion liquid.

To use the hair dye composition, first the first agent and the second agent are mixed. Then, the mixture of the first agent and the second agent is put on a comb or a brush, and applied to hair. The pH of the hair dye composition, namely the mixture of the first agent and the second agent, is preferably 6.5 to 9.5, and more preferably 7.0 to 9.5. If the pH of the hair dye composition is less than 6.5, the hair dye activity may decrease. On the other hand, if the pH of the hair dye composition exceeds 9.5, the skin staining may not be prevented. The pH of the hair dye composition can be adjusted by amounts of an alkaline agent and a pH adjuster contained in the first agent.

The hair dye composition of the present embodiment has the following advantages.

(1) A hair dye composition prepared by mixing the first agent and the second agent contains 1.0 to 5.0% by mass of an ascorbic acid compound and 0.3 to 1.6% by mass of hydrogen peroxide. Further, an alkaline agent is contained in an amount of from 3.0 to 30 mmol per 100 g of the hair dye composition. According to the above, skin staining is prevented without decreasing the hair dye activity of the hair dye.

(2) Preferably, the hair dye composition contains an oxidation dye including a dye intermediate so that the mass ratio of the content of the dye intermediate to the content of the ascorbic acid compound is 0.7 to 1.0. In this case, the effect of preventing skin from staining is further improved.

(3) Preferably, the content of the ascorbic acid compound in the hair dye composition is 1.2 to 4.5% by mass. In this case, the effect of preventing skin from staining is further improved.

(4) Preferably, the pH of the hair dye composition is 6.5 to 9.5. In this case, skin staining is prevented while suppressing reduced hair dye activity.

(5) Preferably, the molar ratio of the content of the alkaline agent to the content of the ascorbic acid compound in the hair dye composition is 0.5 to 2.8. In this case, the effect of preventing skin from staining is further improved.

The embodiment may be altered as below.

In a hair dye composition according to the embodiment, an ascorbic acid compound is contained in the first agent. However, the ascorbic acid compound may be contained in either of the first agent and the second agent. Namely, the ascorbic acid compound may be contained only in the second agent, or contained both in the first agent and the second agent. For the sake of higher storage stability of an ascorbic acid compound, the ascorbic acid compound is preferably contained in the first agent.

EXAMPLES

Next, the embodiment will be described more specifically by way of Examples and Comparative Examples.

First, first and second agents containing the ingredients shown in Tables 1 and 2 were prepared. Next, hair dye compositions of Examples 1 to 14 and Comparative Examples 1 to 9 were prepared respectively by mixing a first agent and a second agent at a mass ratio of 1:1. The figures listed in rows corresponding to the respective ingredients in Tables 1 and 2 stand for the contents of the respective ingredients. The contents are expressed in a unit of % by mass. Each hair dye composition of the Examples and Comparative Examples was applied by a brush to a bundle of white human hair produced by Beaulax Co., Ltd. (hereinafter referred to as "hair bundle"). After the application of the hair dye composition, the hair bundle was left standing at room temperature (25° C.) for 15 minutes. Then, the hair dye composition on the hair bundle was washed out with water, and thereafter the hair bundle was shampooed twice and treated with hair conditioner once. Finally, the hair bundle was dried via a warm air flow and left standing for 1 day, to obtain the hair bundle subjected to the hair dye treatment. Using such hair bundles, the hair dye activity of the respective hair dye compositions of Examples and Comparative Examples were evaluated.

The upper parts of Tables 1 and 2 show the ingredients of the first agents. Reference character (A) of the first agents in Tables 1 and 2 represents oxidation dye ingredients, of which p-phenylenediamine and toluene-2,5-diamine are dye intermediates, and m-aminophenol, 5-amino-o-cresol, and 2,6-diaminopyridine are couplers. In each first agent, in addition to the oxidation dye (A), aqueous ammonia and monoethanolamine as an alkaline agent (B) are contained, and ascorbic acid (D) and other various ingredients are contained. The middle parts of Tables 1 and 2 show the ingredients of the second agents. Each second agent contains hydrogen peroxide (C) and other various ingredients. The lower parts of Tables 1 and 2 respectively show the content of ascorbic acid and the content of hydrogen peroxide in a hair dye composition prepared by mixing a first agent and a second agent, as well as the number of moles of an alkaline agent (B) per 100 g of the hair dye composition, the mass ratio of a dye intermediate, the pH of the hair dye composition during use, and the molar ratio of the alkaline agent. In the Examples, the first agent and the second agent are mixed at a mass ratio of 1:1. Consequently, the content of ascorbic acid in the hair dye composition is half the content of ascorbic acid (D) contained in the first agent. Similarly, the content of hydrogen peroxide in the hair dye composition is half the content of hydrogen peroxide (C) contained in the second agent. "The mass ratio of a dye intermediate" means the mass ratio of the dye intermediate content to the ascorbic acid (D) content in a hair dye composition, namely the amount of dye intermediate/ascorbic acid (D). "The molar ratio of an alkaline agent" means the molar ratio of the alkaline agent (B) content to the ascorbic acid (D) content in a hair dye composition, namely the amount of alkaline agent (B)/ascorbic acid (D). The bottoms of Tables 1 and 2 show the evaluation results of hair dye activity and skin staining.

<Hair Dye Activity>

The L*a*b* values ($L_1$, $a_1$ and $b_1$) of the hair bundle subjected to the hair dyeing treatment with each hair dye composition as described above were measured by a spectrophotometer (Model: CM-508d produced by Minolta Co., Ltd.). From the L*a*b* values of an untreated hair bundle and the L*a*b* values of each hair bundle after the hair dye treatment, the color difference ($\Delta E_1$) between the untreated hair bundle and the hair bundle after the hair dye treatment was calculated according to the following expression (1).

$$\Delta E_1 = \{(L_1-L_0)^2 + (a_1-a_0)^2 + (b_1-b_0)^2\}^{1/2} \ldots \quad (1)$$

In the expression (1), $L_1$, $a_1$, and $b_1$ represent respectively L* value, a* value, and b* value of each hair bundle after the hair dye treatment, and $L_0$, $a_0$, and $b_0$ represent respectively L* value, a* value, and b* value of the untreated hair bundle. At the bottoms of Tables 1 and 2, the value of the color difference ($\Delta E_1$) between the untreated hair bundle and each hair bundle after the hair dye treatment is shown as hair dye activity ($\Delta E$).

<Skin Staining Prevention Effect>

Each of the hair dye composition was applied to an upper arm part, left standing for 30 min, and then washed out. The L value of the upper arm part was measured by a spectrophotometer (Model: CM-508d produced by Minolta Co., Ltd.). From the L value of the upper arm part before application of the hair dye composition and the L value of the upper arm part after application and washing out of the hair dye composition, the $\Delta L^*$ value was calculated. If staining of the upper arm part is weak, the $\Delta L^*$ value gives a value close to 0, but if staining of the upper arm part is strong, the $\Delta L^*$ value gives a value higher than 0. Accordingly, in this evaluation, if the $\Delta L^*$ value is 0 or higher and less than 1.5, the rating was ++; if the value is 1.5 or higher and less than 2.5, the rating was +; if the value is 2.5 or higher and less than 3.5, the rating was ±; if the value is 3.5 or higher and less than 4.5, the rating was −; and if the value is 4.5 or higher, the rating was −−. At the bottoms of Tables 1 and 2, the evaluation results of the skin staining are shown together with those of the hair dye activity ($\Delta E$). FIG. 1 shows the photographs of upper arm parts, which were respectively applied with hair dye compositions and then washed out, according to Example 1 (rated ++), Example 6 (rated +), Example 9 (rated ±), Comparative Example 6 (rated −), and Comparative Example 7 (rated −−).

TABLE 1

| Ingredients (Hair dye composition) | Example 1 | Example 2 | Example 3 | Example 4 | Example 5 | Example 6 | Example 7 |
|---|---|---|---|---|---|---|---|
| First Agent | | | | | | | |
| stearyl alcohol | 10 | 10 | 10 | 10 | 10 | 10 | 10 |
| POE(30) cetyl ether | 5 | 5 | 5 | 5 | 5 | 5 | 5 |
| POE(2) cetyl ether | 2 | 2 | 2 | 2 | 2 | 2 | 2 |

TABLE 1-continued

|  | Ingredients | | | | | | | |
|---|---|---|---|---|---|---|---|---|
|  | stearyl trimethyl ammonium chloride | 1 | 1 | 1 | 1 | 1 | 1 | 1 |
|  | vaseline | 4 | 4 | 4 | 4 | 4 | 4 | 4 |
|  | EDTA-2Na | 0.2 | 0.2 | 0.2 | 0.2 | 0.2 | 0.2 | 0.2 |
|  | sodium sulfite | 0.1 | 0.1 | 0.1 | 0.1 | 0.1 | 0.1 | 0.1 |
| (A) | p-phenylenediamine | 0.90 | 1.10 | 1.00 | 0.81 | 0.75 | 0.60 | 1.10 |
|  | p-toluene-2,5-diamine | 2.12 | 2.65 | 2.49 | 1.91 | 1.77 | 1.41 | 2.65 |
|  | m-aminophenol | 0.25 | 0.31 | 0.29 | 0.23 | 0.21 | 0.17 | 0.31 |
|  | 5-amino-o-cresol | 0.10 | 0.13 | 0.12 | 0.09 | 0.08 | 0.07 | 0.13 |
|  | 2,6-diaminopyridine | 0.20 | 0.25 | 0.23 | 0.18 | 0.17 | 0.13 | 0.25 |
| (D) | ascorbic acid | 4 | 4 | 4 | 4 | 4 | 4 | 4 |
| (B) | 28% aqueous ammonia | 1.5 | 0.5 | 1 | 2 | 2.5 | 3.5 | 3.5 |
|  | 70% monoethanolamine | 0 | 0 | 0 | 0 | 0 | 0 | 0 |
|  | purified water | balance | balance | balance | balance | balance | balance | balance |
|  | Total | 100 | 100 | 100 | 100 | 100 | 100 | 100 |
|  | Second Agent | | | | | | | |
| (C) | hydrogen peroxide | 2 | 2 | 2 | 2 | 2 | 2 | 1 |
|  | sodium stannate | 0.1 | 0.1 | 0.1 | 0.1 | 0.1 | 0.1 | 0.1 |
|  | EDTA | 0.2 | 0.2 | 0.2 | 0.2 | 0.2 | 0.2 | 0.2 |
|  | cetanol | 5 | 5 | 5 | 5 | 5 | 5 | 5 |
|  | POE(2) cetyl ether | 1 | 1 | 1 | 1 | 1 | 1 | 1 |
|  | stearyl trimethyl ammonium chloride | 0.3 | 0.3 | 0.3 | 0.3 | 0.3 | 0.3 | 0.3 |
|  | purified water | balance | balance | balance | balance | balance | balance | balance |
|  | Total | 100 | 100 | 100 | 100 | 100 | 100 | 100 |
|  | Content of ascorbic acid in hair dye composition (% by mass) | 2 | 2 | 2 | 2 | 2 | 2 | 2 |
|  | Content of hydrogen peroxide in hair dye composition (% by mass) | 1 | 1 | 1 | 1 | 1 | 1 | 0.5 |
|  | Number of moles of alkaline agent per 100 g of hair dye composition (mmol) | 12 | 4.1 | 8.2 | 16 | 21 | 29 | 29 |
|  | Mass ratio of dye intermediate | 0.8 | 0.9 | 0.9 | 0.7 | 0.6 | 0.5 | 0.9 |
|  | pH of hair dye composition during use | 7.3 | 6 | 6.5 | 8.5 | 9 | 9.4 | 9.4 |
|  | Molar ratio of alkaline agent | 1.1 | 0.4 | 0.7 | 1.4 | 1.8 | 2.5 | 2.5 |
|  | Evaluation | | | | | | | |
|  | Hair dye activity (ΔE) | 51.3 | 48.0 | 50.7 | 52.0 | 52.2 | 52.5 | 50.8 |
|  | Skin staining prevention effect | ++ | ++ | ++ | ++ | + | + | ++ |

| Ingredients (Hair dye composition) | Example 8 | Example 9 | Example 10 | Example 11 | Example 12 | Example 13 | Example 14 |
|---|---|---|---|---|---|---|---|
| First Agent | | | | | | | |
| stearyl alcohol | 10 | 10 | 10 | 10 | 10 | 10 | 10 |
| POE(30) cetyl ether | 5 | 5 | 5 | 5 | 5 | 5 | 5 |
| POE(2) cetyl ether | 2 | 2 | 2 | 2 | 2 | 2 | 2 |
| stearyl trimethyl ammonium chloride | 1 | 1 | 1 | 1 | 1 | 1 | 1 |
| vaseline | 4 | 4 | 4 | 4 | 4 | 4 | 4 |
| EDTA-2Na | 0.2 | 0.2 | 0.2 | 0.2 | 0.2 | 0.2 | 0.2 |
| sodium sulfite | 0.1 | 0.1 | 0.1 | 0.1 | 0.1 | 0.1 | 0.1 |
| (A) p-phenylenediamine | 0.81 | 0.81 | 0.60 | 1.10 | 1.10 | 0.90 | 0.95 |
| p-toluene-2,5-diamine | 1.91 | 1.91 | 1.41 | 2.65 | 2.65 | 2.12 | 2.28 |
| m-aminophenol | 0.23 | 0.23 | 0.17 | 0.31 | 0.31 | 0.25 | 0.27 |
| 5-amino-o-cresol | 0.09 | 0.09 | 0.07 | 0.13 | 0.13 | 0.10 | 0.11 |
| 2,6-diaminopyridine | 0.18 | 0.18 | 0.13 | 0.25 | 0.25 | 0.20 | 0.21 |
| (D) ascorbic acid | 4 | 4 | 3 | 8 | 10 | 4 | 4 |
| (B) 28% aqueous ammonia | 1.5 | 1.5 | 1.5 | 3.5 | 1.5 | 0 | 0 |
| 70% monoethanolamine | 0 | 0 | 0 | 0 | 0 | 4 | 5 |
| purified water | balance | balance | balance | balance | balance | balance | balance |
| Total | 100 | 100 | 100 | 100 | 100 | 100 | 100 |
| Second Agent | | | | | | | |
| (C) hydrogen peroxide | 2.5 | 3 | 2 | 2 | 2 | 2 | 2 |
| sodium stannate | 0.1 | 0.1 | 0.1 | 0.1 | 0.1 | 0.1 | 0.1 |
| EDTA | 0.2 | 0.2 | 0.2 | 0.2 | 0.2 | 0.2 | 0.2 |
| cetanol | 5 | 5 | 5 | 5 | 5 | 5 | 5 |
| POE(2) cetyl ether | 1 | 1 | 1 | 1 | 1 | 1 | 1 |
| stearyl trimethyl ammonium chloride | 0.3 | 0.3 | 0.3 | 0.3 | 0.3 | 0.3 | 0.3 |
| purified water | balance | balance | balance | balance | balance | balance | balance |
| Total | 100 | 100 | 100 | 100 | 100 | 100 | 100 |
| Content of ascorbic acid in hair dye composition (% by mass) | 2 | 2 | 1.5 | 4 | 5 | 2 | 2 |
| Content of hydrogen peroxide in hair dye composition (% by mass) | 1.25 | 1.5 | 1 | 1 | 1 | 1 | 1 |
| Number of moles of alkaline agent per 100 g of hair dye composition (mmol) | 12 | 12 | 12 | 29 | 12 | 23 | 29 |

TABLE 1-continued

| | | | | | | | |
|---|---|---|---|---|---|---|---|
| Mass ratio of dye intermediate | 0.7 | 0.7 | 0.7 | 0.5 | 0.4 | 0.8 | 0.8 |
| pH of hair dye composition during use | 7.3 | 7.3 | 8.4 | 8.4 | 7.1 | 9.3 | 9.5 |
| Molar ratio of alkaline agent | 1.1 | 1.1 | 1.4 | 1.3 | 0.4 | 2.0 | 2.5 |
| Evaluation | | | | | | | |
| Hair dye activity (ΔE) | 49.3 | 50.6 | 50.5 | 50.9 | 45.7 | 51.6 | 51.6 |
| Skin staining prevention effect | ++ | ± | ++ | ++ | ++ | ++ | ± |

TABLE 2

| Ingredients (Hair dye composition) | Comparative Example 1 | Comparative Example 2 | Comparative Example 3 | Comparative Example 4 | Comparative Example 5 | Comparative Example 6 | Comparative Example 7 | Comparative Example 8 | Comparative Example 9 |
|---|---|---|---|---|---|---|---|---|---|
| First Agent | | | | | | | | | |
| stearyl alcohol | 10 | 10 | 10 | 10 | 10 | 10 | 10 | 10 | 10 |
| POE(30) cetyl ether | 5 | 5 | 5 | 5 | 5 | 5 | 5 | 5 | 5 |
| POE(2) cetyl ether | 2 | 2 | 2 | 2 | 2 | 2 | 2 | 2 | 2 |
| stearyl trimethyl ammonium chloride | 1 | 1 | 1 | 1 | 1 | 1 | 1 | 1 | 1 |
| vaseline | 4 | 4 | 4 | 4 | 4 | 4 | 4 | 4 | 4 |
| EDTA-2Na | 0.2 | 0.2 | 0.2 | 0.2 | 0.2 | 0.2 | 0.2 | 0.2 | 0.2 |
| sodium sulfite | 0.1 | 0.1 | 0.1 | 0.1 | 0.1 | 0.1 | 0.1 | 0.1 | 0.1 |
| (A) p-phenylenediamine | 1.10 | 0.60 | 0.60 | 0.60 | 1.10 | 0.77 | 0.75 | 0.77 | 1.10 |
| p-toluene-2,5-diamine | 2.65 | 1.41 | 1.41 | 1.41 | 2.65 | 1.82 | 1.77 | 1.82 | 2.65 |
| m-aminophenol | 0.31 | 0.17 | 0.17 | 0.17 | 0.31 | 0.21 | 0.21 | 0.21 | 0.31 |
| 5-amino-o-cresol | 0.13 | 0.07 | 0.07 | 0.07 | 0.13 | 0.09 | 0.08 | 0.09 | 0.13 |
| 2,6-diaminopyridine | 0.25 | 0.13 | 0.13 | 0.13 | 0.25 | 0.17 | 0.17 | 0.17 | 0.25 |
| (D) ascorbic acid | 4 | 4 | 4 | 3 | 4 | 4 | 4 | 3.5 | 4 |
| (B) 28% aqueous ammonia | 0 | 4 | 4.5 | 4 | 3.5 | 1.5 | 1.5 | 1.5 | 0 |
| 70% monoethanolamine | 0 | 0 | 0 | 0 | 0 | 0 | 0 | 0 | 6 |
| purified water | balance | balance | balance | balance | balance | balance | balance | balance | balance |
| Total | 100 | 100 | 100 | 100 | 100 | 100 | 100 | 100 | 100 |
| Second Agent | | | | | | | | | |
| (C) hydrogen peroxide | 2 | 2 | 2 | 2 | 0.3 | 3.5 | 4 | 3.5 | 2 |
| sodium stannate | 0.1 | 0.1 | 0.1 | 0.1 | 0.1 | 0.1 | 0.1 | 0.1 | 0.1 |
| EDTA | 0.2 | 0.2 | 0.2 | 0.2 | 0.2 | 0.2 | 0.2 | 0.2 | 0.2 |
| cetanol | 5 | 5 | 5 | 5 | 5 | 5 | 5 | 5 | 5 |
| POE(2) cetyl ether | 1 | 1 | 1 | 1 | 1 | 1 | 1 | 1 | 1 |
| stearyl trimethyl ammonium chloride | 0.3 | 0.3 | 0.3 | 0.3 | 0.3 | 0.3 | 0.3 | 0.3 | 0.3 |
| purified water | balance | balance | balance | balance | balance | balance | balance | balance | balance |
| Total | 100 | 100 | 100 | 100 | 100 | 100 | 100 | 100 | 100 |
| Content of ascorbic acid in hair dye composition (% by mass) | 2 | 2 | 2 | 1.5 | 2 | 2 | 2 | 1.75 | 2 |
| Content of hydrogen peroxide in hair dye composition (% by mass) | 1 | 1 | 1 | 1 | 0.15 | 1.75 | 2 | 1.75 | 1 |
| Number of moles of alkaline agent per 100 g of hair dye composition (mmol) | 0.0 | 33 | 37 | 33 | 29 | 12 | 12 | 12 | 34 |
| Mass ratio of dye intermediate | 0.9 | 0.5 | 0.5 | 0.7 | 0.9 | 0.6 | 0.6 | 0.7 | 0.9 |
| pH of hair dye composition during use | 5.5 | 9.5 | 9.6 | 9.4 | 9.4 | 7.2 | 7.2 | 7.3 | 9.7 |
| Molar ratio of alkaline agent | 0.0 | 2.9 | 3.3 | 3.9 | 2.5 | 1.1 | 1.1 | 1.2 | 3.0 |
| Evaluation | | | | | | | | | |
| Hair dye activity (ΔE) | 39.5 | 51.4 | 51.7 | 52.0 | 30.7 | 50.5 | 50.3 | 51.1 | 51.0 |
| Skin staining prevention effect | ++ | −− | −− | − | ++ | − | −− | − | −− |

As shown in Table 1, the hair dye activity (ΔE) for each of the hair dye compositions according to the Examples was higher than 45. Similarly, with respect to skin staining, the ΔL* values were less than 3.5. As indicated by these results, the hair dye compositions according to the Examples exhibited superior hair dye activity and skin staining prevention effect.

As shown in Table 2, the hair dye composition according to Comparative Example 1, which did not contain an alkaline agent, exhibited lower hair dye activity (ΔE) compared to all of the Examples. Meanwhile, the hair dye compositions according to Comparative Examples 2 to 4 and 9, which contained an alkaline agent more than 30 mmol/100 g, exhibited a lower skin staining prevention effect compared to all of the Examples. Further, the hair dye composition according to Comparative Example 5, which contained hydrogen peroxide less than 0.3% by mass, exhibited lower hair dye activity (ΔE) compared to all of the Examples. The hair dye compositions according to Comparative Examples 6 to 8, which contained hydrogen peroxide more than 1.6% by mass, exhibited a lower skin staining prevention effect compared to all of the Examples.

As obvious from the photographs in FIG. 1, the hair dye compositions according to Examples 1, 6 and 9 scarcely dyed an upper arm part. More specifically, in Example 1 dyeing did not occur. In Example 6, there was no recognizable dyeing. In Example 9, there was slight dyeing at an upper arm part (center of the photograph), but staining the skin was at an acceptable level. On the contrary, in Comparative Examples 6 and 7, there was clearly recognizable dyeing at an upper arm part (center of the photographs). Consequently, the afore-described evaluation results concerning skin staining according to a spectrophotometer were supported by the photographs of FIG. 1.

The invention claimed is:
1. A hair dye composition comprising:
a first agent containing an oxidation dye and an alkaline agent; and
a second agent containing hydrogen peroxide, the hair dye composition being used after mixing the first agent and the second agent,
wherein the hair dye composition contains an ascorbic acid compound and the hydrogen peroxide in amounts of from 1.0 to 5.0% by mass and from 0.3 to 1.6% by mass, respectively, and
wherein the alkaline agent is contained in an amount of from 3.0 to 30 mmol per 100 g of the hair dye composition.

2. The hair dye composition according to claim 1, wherein the oxidation dye contains a dye intermediate, wherein the hair dye composition has a mass ratio of dye intermediate content to ascorbic acid compound content in the hair dye composition of from 0.7 to 1.0.

3. The hair dye composition according to claim 1, wherein the ascorbic acid compound is contained in the hair dye composition in an amount of from 1.2 to 4.5% by mass.

4. The hair dye composition according to claim 1, wherein the hair dye composition has a pH of from 6.5 to 9.5.

5. The hair dye composition according to claim 1, wherein the hair dye composition has a molar ratio of alkaline agent content to ascorbic acid compound content in the hair dye composition of from 0.5 to 2.8.

* * * * *